(12) United States Patent
Reddy et al.

(10) Patent No.: US 8,268,368 B2
(45) Date of Patent: Sep. 18, 2012

(54) HERBAL FORMULATIONS FOR THE MANAGEMENT OF CHRONIC ULCERS AND WOUNDS

(75) Inventors: N. B. Baktha Reddy, Kelambakkam (IN); Vilambi NRK Reddy, Trichy (IN); Anil M. Torgalkar, Cranbury, NJ (US)

(73) Assignee: APPTEC, Inc., Cranbury, NJ (US)

(*) Notice: Subject to any disclaimer, the term of this patent is extended or adjusted under 35 U.S.C. 154(b) by 0 days.

(21) Appl. No.: 12/925,647

(22) Filed: Oct. 26, 2010

(65) Prior Publication Data

US 2011/0097424 A1   Apr. 28, 2011

Related U.S. Application Data

(60) Provisional application No. 61/279,795, filed on Oct. 26, 2009.

(51) Int. Cl.
*A61K 36/889* (2006.01)
(52) U.S. Cl. .................. 424/727; 424/725; 424/401
(58) Field of Classification Search ........................ None
See application file for complete search history.

(56) References Cited

U.S. PATENT DOCUMENTS

2002/0001600 A1   1/2002   Oldham et al.

FOREIGN PATENT DOCUMENTS

WO   2008072256 A1   6/2008

OTHER PUBLICATIONS

Agasthiyar (Agathiyar vaithya vallanthi 600, Pub&Ed Deenadhayalu muthaliar, Chennai (1924)).*
Nayak (Phytotherapy Research (2007), vol. 21, pp. 827-831).*
http://www.ewg.org/skindeep/ingredient.php?ingred06=703508—accessed Aug. 2011.*
"Karanja" composition (The Ayurvedic Pharmacopoeia of India—Part I, vol. I, End. 1st, Reprinted—2001, Govt of India, Ministry of Health & Family Welfare, Deptt. Of I.S.M. & H., New Delhi, p. 63).*
"Vranahar Taila" composition (Vaidyamanorama: Central Council for Research in Ayurveda & Siddha, Govt. of India, New Delhi, 2005, pp. 104).*
Priya, K. Shanmuga, Healing potential of Datura alba on burn wounds in albino rats, Journal of Ethnopharmacology vol. 83, 193-199, 2002, India.

* cited by examiner

*Primary Examiner* — Susan Hoffman
(74) *Attorney, Agent, or Firm* — Stanley H. Kremen

(57) ABSTRACT

The invention describes ointments, creams and oils formulated from herbal compositions that are suitable for the management of skin wounds, such as chronic skin ulcers, as, for example, diabetic ulcers and pressure ulcers, and for providing bleeding control for cuts and wounds. The compositions contain extracts of two or more of *Pongamia pinnata*, *Lawsonia alba*, *Datura alba* and *Cocos nucifera*.

4 Claims, No Drawings

HERBAL FORMULATIONS FOR THE MANAGEMENT OF CHRONIC ULCERS AND WOUNDS

CROSS-REFERENCE TO RELATED APPLICATIONS

The present application claims priority benefit under 35 U.S.C. sctn. 119(e) of U.S. Provisional Patent Application Ser. No. 61/279,795 filed Oct. 26, 2009. The disclosures of this application are incorporated herein by reference in their entirety.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISK APPENDIX

Not applicable.

BACKGROUND OF THE INVENTION

Field of the Invention

The present invention relates to herbal formulations that are suitable for the management of skin wounds, such as chronic skin ulcers, as, for example, diabetic ulcers and pressure ulcers, and for providing bleeding control for cuts and wounds.

The present invention relates to the discovery that extracts of two or more of *Pongamia pinnata, Lawsonia alba, Datura alba* and *Cocos nucifera*, when used in the compositions of this invention, produce unexpectedly effective results in the management of skin wounds, such as chronic ulcers.

The herbal compositions are low in cost to prepare, require fewer dressings than the current state of the art treatments, and are clinically proven to be safe and extremely effective.

BRIEF SUMMARY OF THE INVENTION

An object of the invention is to provide ointment, cream, and oil formulations comprising herbal compositions that, when used topically in an effective amount, provide a treatment for chronic ulcers. The herbal compositions comprise an effective amount of at least two of the herbal extracts: *Pongamia pinnata, Lawsonia alba, Datura alba* and *Cocos nucifera*, and one or more pharmaceutically or cosmetically acceptable excipients suitable for topical use.

Another object of the invention is to provide a method of healing chronic wounds, such as chronic ulcers, including diabetic ulcers, by using the ointment, cream, and oil formulations described above.

BRIEF DESCRIPTION OF THE SEVERAL VIEWS OF THE DRAWING

Not applicable.

DETAILED DESCRIPTION OF THE INVENTION

It is believed that, based upon the description herein, one skilled in the art can utilize the present invention to its fullest extent. The following embodiments are to be construed as being merely illustrative, and not limiting of the remainder of the disclosure in any way whatsoever.

Unless otherwise defined, all technical and scientific terms used herein have the same meaning as commonly understood by one of ordinary skill in the art to which the invention belongs. Also, all publications, patent applications, patents and other references mentioned herein are incorporated by reference in their entirety. Unless otherwise indicated, a percentage refers to a percentage by weight of the whole (i.e., % (W/W).

DEFINITIONS

In this document, the term "herb" refers to a wide range of plants in addition to herbaceous perennials, including trees, shrubs, annuals, vines, and more primitive plants, such as ferns, mosses, algae, lichens, and fungi. Herbs are valued for their flavor, fragrance, medicinal and healthful qualities, economic and industrial uses, pesticidal properties, and coloring materials (dyes).

The term "chronic ulcer" refers to a persistent ulcer with fibrous scar tissue in the floor of the ulcer. Some examples of chronic ulcers are diabetic ulcers and pressure ulcers, also called decubitus ulcers.

As used herein, "management of ulcers" means to reduce or prevent skin ulcers or bleeding.

As used herein, "composition" means a composition suitable for administration to the skin.

As used herein, "a safe and effective amount" means an amount of the herbal extracts, or of the composition, sufficient to induce wound healing, but low enough to avoid serious side effects. The safe and effective amount of the compounds or composition will vary with the area being treated, the age, health and skin type of the patient, the duration and nature of the treatment, the specific compound or composition employed, the particular carrier utilized, and like factors.

*Pongamia pinnata* is also known as pongam, karanja, karang. It is indigenous to India and Burma/Myanmar and is one of the few nitrogen fixing trees (NFTS) to produce seeds containing 30-40% oil. It is often planted as an ornamental and shade tree but is being considered as an alternative source for biodiesel. The seeds and the oil obtained from the seeds are used in some embodiments of this invention.

*Lawsonia alba* (CAS 83-72-7) is commonly known as henna. The plant is indigenous to Africa. The leaves of this plant are used in embodiments of this invention.

*Datura alba* is also known as the thorn apple. The leaves have been shown to be useful in treating burn wounds in rats. The leaves of *Datura alba* are used in some embodiments of this invention.

*Cocos nucifera* or coconut. An extract prepared from the oil of the pressed nut is used in some embodiments of this invention.

NaturalQ is the tradename for a product for treating skin ulcers, the composition of which is within the bounds set by this invention.

Erythema, as used herein, is defined as a redness of skin or a rash.

qs is defined as a quantity sufficient to make the whole 100%.

Formulations

An object of this invention is to provide an ointment for topical use in the management of chronic ulcers, diabetic ulcers, and the management of bleeding in cuts and wounds, comprised of at least two of the following ingredients present in the formulation in the given amounts:

An extract of *Pongamia pinnata* present in the range of 2 to 20%

An extract of *Lawsonia alba* present in the range of 5 to 15%

An extract of *Datura alba* in the range of 2 to 20%

An extract of *Cocos nucifera* in the range of 20 to 60%

An object of this invention is to provide a preferred formulation for an ointment for topical use in the management of chronic ulcers, diabetic ulcers, and the management of bleeding in cuts and wounds comprised of at least two of the following ingredients present in the formulation in the given amounts:

10% by weight of an extract of *Pongamia pinnata*
10% of an extract of *Lawsonia alba*
10% of an extract of *Datura alba*
40% of an extract of *Cocos nucifera*

Another object of this invention is to provide a cream for topical use in the management of pressure ulcers, the oil phase of which is comprised of at least two of the following ingredients present in the formulation in the given amounts:

An extract of *Pongamia pinnata* present in the range of 0.5 to 2.5%

An extract of *Lawsonia alba* present in the range of 0.5 to 1.5%

An extract of *Datura alba* in the range of 0.2 to 1%

An extract of *Cocos nucifera* in the range of 3.0 to 10.0%

The preferred formulation for a cream to be used in the management of pressure ulcers, the oil phase of which is comprised of at least two of the following ingredients present in the formulation in the given amounts:

1.5% by weight of an extract of *Pongamia pinnata*
1.0% by weight of an extract of *Lawsonia alba*
0.6% by weight of an extract of *Datura alba*
7.0% by weight of an extract of *Cocos nucifera*

An object of this invention is to provide an oil for topical use in providing bleeding control, comprised of at least two of the following ingredients present in the formulation in the given amounts:

An extract of *Pongamia pinnata* present in the range of 5 to 25%

An extract of *Lawsonia alba* present in the range of 5 to 15%

An extract of *Datura alba* in the range of 2 to 10%

An extract of *Cocos nucifera* qs (quantity sufficient)

An object of this invention is to provide a preferred formulation for an oil to provide bleeding control, comprised of at least two of the ingredients:

15% by weight of an extract of *Pongamia pinnata*
10% of an extract of *Lawsonia alba*
6% of an extract of *Datura alba*
qs of an extract of *Cocos nucifera*

The ointment formulations of this invention include pharmaceutically acceptable GRAS (Generally Regarded As Safe) ingredients such as beeswax, paraffin (liquid, soft and hard), petroleum jelly and other standard ointment bases or equivalents to optimize use characteristics, such as consistency, spreadability, and others, manufacturability and stability.

The cream formulations of this invention may include pharmaceutically acceptable GRAS (Generally Regarded As Safe) ingredients, such as one or more emulsifying agents, liquid paraffin, humectants and water.

The oil formulation comprising a composition of this invention for topical use may include pharmaceutically acceptable ingredients, such as fragrance oils.

The use of the herbal compositions of the present invention is illustrated by the following examples:

Example 1

Clinical Evaluation of the NaturalQ Ointment Formulation in the Management of Chronic Ulcers Safety and Effectiveness Study 1 Summary A clinical study to evaluate the safety and effectiveness of an herbal formulation in improving the clinical condition of wound care patients with chronic ulcers was successfully completed. The study protocol along with the Informed consent form (ICF), case report forms (CRF), principal investigator's curriculum vitae (C.V.), and relevant safety study reports/literature were submitted for review and approval to a duly constituted Ethics Committee (EC) before initiation of the study. The study was conducted as per Good Clinical Practice (GCP) guidelines for the ethical conduct of clinical studies.

A preferred composition of this invention, NaturalQR Ointment for chronic ulcers, is a formula in an ointment base including extracts of the following herbs used in clinical practice in India by traditional doctors: *Pongamia pinnata, Lawsonia alba, Datura alba* and *Cocos nucifera*.

12 subjects (18 treatment sites) completed the 8 week study. No adverse events were reported during the conduct of the study.

Subject inclusion criteria included: all the subjects are known ulcer patients including members of both sexes; are capable of understanding and signing (accepting) an informed consent form; are more than 18 years of age; are medically stable and possess chronic ulcers.

Subject exclusion criteria included: nursing mothers; a history of sexually transmitted disease; a history of high blood pressure; a history of cardiovascular disease (MI in the past year); a history of fainting, arrhythmia or irregular pulse; a history of drug, substance or alcohol abuse; the use of alcohol or drugs within 48 hours prior to and during the study participation; any psychological condition that could influence the conduct of the study or interpretation of results; malnutrition (BMI<19); the use of another investigational medication/treatment in the past 30 days; any condition, which, in the opinion of the principal investigator, would place the subject at risk or influence the conduct of the study or interpretation of results.

The study patients were scheduled to and visited the clinic at T0, T2d, T4d, T6d, T8d, T10d, T12d, T14d, T3w, T4w, T6w, T7w and T8w. During each visit, the treatment site(s) was cleaned with hydrogen peroxide; a photo was taken; a clinical examination was done and the site was scored for erythema, amount of discharge, the size of wound and the margin of wound. NaturalQ ointment was applied to the treatment site, spread to cover the site and then the site was covered with a gauze bandage.

The safety of the herbal formulation was assessed by monitoring each subject's vital signs (temperature, BP-systolic, BP-diastolic) during every visit and by haemogram (TC, DC-P, DC-L, DC-E, DC-M, RBC and Hb)/LFT (SGOT, SGPT and serum bilirubin)/RFT (serum creatinine, serum urea) measurements at the beginning and end of the study. The statistical analysis of the safety data clearly suggests that no toxic effects were observed with the application of the herbal formulation and all the values observed were well within the clinically accepted range.

The efficacy of the herbal formulation was assessed by trained personnel at each visit, who scored erythema, discharge, wound size and the condition of the margin of the wounds.

Erythema scoring was done by an expert dermatologist at every visit. The results of erythema measurements were scored as follows: none (0), very slight (1), well defined (2), moderate (3), or severe (4). The results of the analysis of the erythema scores during the treatment are presented below in Table 1-1.

TABLE 1-1

Chronic Ulcer-Erythema

| Time (days) | Mean | Variance |
|---|---|---|
| 0 | 0.333 | 0.235 |
| 2 | 0.111 | 0.105 |
| 4 | 0.278 | 0.212 |
| 6 | 0.056 | 0.056 |
| 8 | 0.000 | 0.000 |
| 1 way ANOVA F-statistic | 2.976 | |
| P-value | 0.024 | |

A regular one-way ANOVA was also used to analyze the erythema data at different time points to examine the time effects. The data clearly indicates that in general, the observation of erythema at the treatment site(s) decreased with time. The highest mean erythema score of 0.333 was observed at time T0 and decreased to 0 in 8 days. The decrease was found to be statistically significant (p-value=0.024). In summary, the use of the herbal ointment was found to decrease erythema at the treatment site(s) and, after about 8 days, no erythema was observed at the treatment site(s).

The scoring for discharge at the treatment site was done by a trained investigator at every visit. The results of the discharge measurements were scored as follows: No (0), Mild (1), Moderate (2), or Severe (3). The results of the analysis of the discharge scores for the herbal treatment is presented below in Table 1-2.

TABLE 1-2

Chronic Ulcers-Discharge

| Time | Mean | Variance |
|---|---|---|
| 0 d | 0.889 | 1.281 |
| 2 d | 0.278 | 0.212 |
| 4 d | 0.111 | 0.105 |
| 6 d | 0.000 | 0.000 |
| 1-way ANOVA F-statistic | 7.080 | |
| P-value | 0.0003 | |

A regular one-way ANOVA was also used to analyze the discharge data at different time points to examine the effects over time. The data clearly indicates that, in general, the observation of discharge at the treatment site(s) decreased with time. The highest mean discharge score of 0.889 was observed at time T0 and decreased to 0 in 6 days. The decrease was found to be statistically significant (p-value=0.0003.) In summary, the use of the herbal ointment in a formulation included in this invention was found to decrease discharge at the treatment site(s) and in less than 6 days the discharge was completely stopped at all treatment site(s).

Wound size measurements were done at each treatment site by a trained investigator at every visit. The size of the wound was measured in $cm^2$ and then normalized to 100 at day 0. The results of the analysis of the wound size measurements for the herbal treatment is presented below in Table 1-3.

TABLE 1-3

Chronic Ulcers-Wound Size

| Time (days) | Mean | Variance |
|---|---|---|
| 0 | 100 | 0 |
| 4 | 58.13 | 1231.52 |
| 6 | 42.82 | 1260.53 |
| 8 | 35.29 | 1152.51 |
| 10 | 30.96 | 727.68 |
| 12 | 22.52 | 428.59 |
| 14 | 24.13 | 486.80 |
| 21 | 28.26 | 875.78 |
| 28 | 24.58 | 314.46 |
| 35 | 20.45 | 211.74 |
| 42 | 12.76 | 24.46 |
| 49 | 8.03 | 3.09 |
| 56 | 12.67 | 28.67 |
| 1-way ANOVA-statistic | 12.44 | |
| P-value | 2.3E−17 | |

A regular one-way ANOVA was also used to analyze the wound size data at different time points to examine the effects of treatment over time. The data clearly indicates that, in general, the size of the wound at the treatment site(s) decreased with time. The size of the wound decreased with the herbal treatment to approximately 12% of the initial size in 6-8 weeks. The decrease was found to be statistically significant (p-value=2.3E-17). In summary, the use of the herbal ointment was found to statistically significantly decrease the size of the wound at treatment site(s) and in about 8 weeks the size of the wound decreased with the herbal treatment to 12% of the initial size before treatment.

Scoring for the margin of the wound at the treatment site was done by a trained investigator at every visit. The results of the margin of the wound measurements were scored as follows: Regular (0), Irregular (1). The results of the analysis of the margin of wound scores for the herbal treatment is presented below in Table 1-4.

TABLE 1-4

Chronic Ulcers-Margin of Wound

| Time (days) | Mean | Variance |
|---|---|---|
| 0 | 0.500 | 0.265 |
| 2 | 0.333 | 0.235 |
| 4 | 0.222 | 0.183 |
| 6 | 0.111 | 0.105 |
| 8 | 0.059 | 0.059 |
| 10 | 0.059 | 0.059 |
| 12 | 0.059 | 0.059 |
| 14 | 0.000 | 0.000 |
| 1-way ANOVA F-statistic | 4.139 | |
| P-value | 0.0004 | |

A regular one-way ANOVA was also used to analyze the margin of wound data at different time points to examine the effects of treatment over time. The data clearly indicates that, in general, the margin of wound at the treatment site(s) became more regular with time. The highest mean margin of wound score of 0.5 was observed time at T0 and decreased to 0 in 14 days. The decrease was found to be statistically significant (p-value=0.0004). In summary, the use of herbal ointment was found to improve the margin of wounds, which was becoming more regular. In about 14 days the margin of the wounds was found to be regular at all treatment site(s).

Study 1 Results Summary

Overall, it was found that the NaturalQR herbal ointment for chronic ulcers was safe and effective in the treatment of chronic ulcers. The use of the herbal ointment was found to:

decrease erythema at treatment site(s) and in approximately 8 days no erythema was observed at the treatment site(s)

decrease discharge at treatment site(s) and in about 6 days the discharge completely stopped at all treatment site(s)

statistically significantly decrease the size of the wound at treatment site(s). In less than approximately 8 weeks the size of the wound decreased with the treatment to about 12% of the initial size before treatment improve the margin of wounds. The margins became more regular. In approximately 14 days the wound margin was found to be regular at all treatment site(s).

Example 2

Clinical Evaluation of an Herbal Ointment Formulation in the Management of Diabetic Ulcers Safety and Effectiveness Study 2 Summary A clinical study to evaluate the safety and effectiveness of the NaturalQ formulation in improving the clinical condition of wound care patients with diabetic ulcers was successfully completed. The study protocol along with the Informed consent form (ICF), case report forms (CRF), principal investigator's curriculum vitae (C.V.), and relevant safety study reports/literature were submitted for review and approval to a duly constituted ethics committee (EC) before initiation of the study. The study was conducted as per Good Clinical Practice (GCP) guidelines for the ethical conduct of clinical studies.

A preferred formulation of this invention, NaturalQR Ointment for Diabetic Ulcers, is a formula in an ointment base including extracts of the following herbs used in clinical practice in India by traditional doctors: *Pongamia pinnata*, *Lawsonia alba*, *Datura alba* and *Cocos nucifera*.

Ten subjects completed the 8 week study. No adverse events were reported during the conduct of the study.

Subject Inclusion criteria: The study subjects are known diabetic ulcer patients including members of both sexes; are capable of understanding and signing (accepting) an informed consent document; have a history of diabetes; are more than 18 years of age; and medically stable.

Subject exclusion criteria included: nursing mothers; a history of sexually transmitted disease; a history of high blood pressure; a history of cardiovascular disease (MI in the past year); a history of fainting, arrhythmia or irregular pulse; a drug, substance or alcohol abuse; use of alcohol or drugs within 48 hours prior to and during study participation; any psychological condition that would influence the conduct of the study or interpretation of results; malnutrition (BMI<19); use of another investigational medication/treatment in the past 30 days; any condition, which in the opinion of the principal Investigator would place the subject at risk or influence the conduct of the study or interpretation of results.

The study patients were scheduled to and visited the clinic at T0, T2d, T4d, T6d, T8d, T10d, T12d, T14d, T3w, T4w, T6w, T7w and T8w. During each visit, the treatment site(s) was cleaned with hydrogen peroxide; a photo was taken; a clinical examination was conducted and the site was scored for erythema, discharge, the size of wound and the margin of wound. NaturalQ ointment was applied to the treatment site, spread to cover the site, and then the site was covered with a gauze bandage.

Blood sugar was measured for all subjects on Day 0. The mean blood sugar level for all patients was 238 mg/dl (SD: 107 mg/dl), ensuring that all subjects enrolled in the study were diabetic.

The safety of the herbal formulation was assessed by monitoring each subject's vital signs (temperature, BP-systolic, BP-diastolic) during every visit and haemogram (TC, DC-P, DC-L, DC-E, DC-M, RBC and Hb)/LFT (SGOT, SGPT and serum bilirubin)/RFT (serum creatinine, serum urea) measurements at the beginning and end of the study. Statistical analysis of the safety data clearly suggests that no toxic effects were observed with the application of the herbal formulation and all the values observed were well within the clinically accepted range.

The efficacy of the herbal formulation was assessed by trained personnel at each visit, who scored erythema, discharge, wound size and the condition of the margin of the wounds.

Erythema scoring was done by an expert dermatologist at every visit. The results of erythema measurements were scored as follows: none (0), very slight (1), well defined (2), moderate (3), or severe (4). The results of the analysis of the erythema scores during the treatment are presented below in Table 2-1.

TABLE 2-1

Erythema-Diabetic Ulcers

| Time (days) | Mean | Variance |
|---|---|---|
| 0 | 0.7 | 0.46 |
| 8 | 0.4 | 0.49 |
| 14 | 0.1 | 0.10 |
| 21 | 0 | 0.00 |
| 1-way ANOVA F-Statistic | 3.830 | |
| P-value | 0.018 | |

A regular one-way ANOVA was also used to analyze the erythema data at different time points to examine the time effects. The data clearly indicates that in general, the observation of erythema at the treatment site(s) decreased with time. The highest mean erythema score of 0.7 was observed at time T0 and decreased to 0 in 21 days. The decrease was found to be statistically significant (p-value=0.018). In summary, the use of the herbal ointment described in this document was found to decrease erythema at the treatment site(s) and in about 21 days, no erythema was observed at the treatment site(s).

The scoring for discharge at the treatment site was done by a trained investigator at every visit. The results of the discharge measurements were scored as follows: none (0), mild (1), moderate (2), or severe (3). The results of the analysis of the discharge scores for the herbal treatment is presented below in Table 2-2

TABLE 2-2

Discharge-Diabetic Ulcers

| Time (days) | Mean | Variance |
|---|---|---|
| 0 | 1.3 | 0.90 |
| 8 | 0.7 | 0.46 |

TABLE 2-2-continued

Discharge-Diabetic Ulcers

| Time (days) | Mean | Variance |
|---|---|---|
| 14 | 0.4 | 0.27 |
| 21 | 0 | 0.00 |
| 1-way ANOVA F-Statistic P-value | 7.397 0.001 | |

A regular one-way ANOVA was also used to analyze the discharge data at different time points to examine the effects of treatment over time. The data clearly indicates that, in general, the observation of discharge at treatment site(s) decreased with time. The highest mean discharge score of 1.3 was observed at time T0 and decreased to 0 in 21 days. The decrease was found to be statistically significant (p-value=0.001). In summary, the use of the herbal ointment in a formulation of this invention was found to decrease the discharge at the treatment site(s) and in about 21 days the discharge completely stopped at all treatment site(s).

Wound size measurements were done at each treatment site by a trained investigator at every visit. The size of the wound was scored as: −2=increased, −1=slightly Increased, 0=same, 1=slightly decreased, 2=significantly decreased, 3=completely closed. The results of the analysis of the wound size measurements during the treatment is presented below in Table 2-3.

TABLE 2-3

Wound Size-Diabetic Ulcers

| Time (days) | Mean | Variance |
|---|---|---|
| 0 | 0.0 | 0.00 |
| 8 | 0.3 | 0.46 |
| 14 | 1.4 | 0.27 |
| 21 | 1.3 | 0.23 |
| 28 | 1.7 | 0.68 |
| 35 | 1.9 | 0.48 |
| 42 | 2.0 | 0.67 |
| 49 | 2.0 | 0.67 |
| 1-way ANOVA F-Statistic P-value | 12.412 8.16E−10 | |

A regular one-way ANOVA was also used to analyze the wound size data at different time points to examine the effects of the treatment over time. The data clearly indicates that in general, the size of the wound at the treatment site(s) decreased with time. The data clearly suggests that the size of the wound slightly decreased (0.5<mean score<1.5) with the treatment in 2-3 weeks and then significantly decreased in 4-7 weeks (1.5<mean score<2.5). The decrease in wound size was found to be statistically significant (p-value=8.16E-10). In summary, the use of the herbal ointment was found to statistically significantly decrease the size of the wound at treatment site(s) in about 4-7 weeks and in 4 out of 10 patients the wound was completely closed within 4-7 weeks.

Scoring for the margin of wound at the treatment site was done by a trained investigator at every visit. The results of the margin of wound measurements were scored as follows: Regular (0), Irregular (1). The results of the analysis of the margin of wound scores for the herbal treatment is presented below in Table 2-4.

TABLE 2-4

Margin of Wounds-Diabetic Ulcers

| Time (days) | Mean | Variance |
|---|---|---|
| 0 | 0.8 | 0.18 |
| 8 | 0.5 | 0.28 |
| 14 | 0 | 0.00 |
| 1-way ANOVA F-Statistic P-value | 10.756 0.0004 | |

A regular one-way ANOVA was also used to analyze the margin of wound data at different time points to examine the effects of treatment over time. The data clearly indicates that, in general, the margin of the wound at the treatment site(s) became more regular with time. The highest mean margin of the wound score of 0.8 was observed at time T0 and decreased to 0 in 14 days. The decrease was found to be statistically significant (p-value=0.0004). In summary, the use of the herbal ointment of this invention was found to improve the margin of wounds, which was becoming more regular. In approximately 14 days the margin of wounds was found to be regular at all treatment site(s).

Study 2 Results Summary

Overall, it was found that the NaturalQR herbal ointment for diabetic ulcers was safe and effective in the treatment of diabetic ulcers. The use of the herbal ointment was found to:
statistically significantly decrease erythema (P-value=0.018) at the treatment site(s). In approximately 21 days no erythema was observed at the treatment site(s)
statistically significantly decrease the amount of discharge (P-value=0.001) at the treatment site(s). In about 21 days the discharge completely stopped at all treatment site(s)
statistically significantly decrease the size of the wound (P-value=8.16E-10) at the treatment site(s) in approximately 4-7 weeks. In 4 out of 10 patients the wound was completely closed within 4-7 weeks
statistically significantly improve the margin of the wounds. The margin became more regular (P-value=0.0004) and in about 14 days the margin of the wounds was found to be regular at all treatment site(s).

Other modifications and variations of the present invention will become apparent to those skilled in the art from an examination of the above specification and examples. Therefore, other variations of the present invention may be made which fall within the scope of the appended claims, even though such variations were not specifically discussed above.

We claim:

1. An ointment for topical use in humans in the management of chronic ulcers, diabetic ulcers, and the management of bleeding in cuts and wounds, comprising:
    a) an extract of *Pongamia pinnata* present in the amount of 10% by weight;
    b) an extract of *Lawsonia alba* present in the amount of 10% by weight;
    c) an extract of *Datura alba* present in the amount of 10% by weight; and
    d) an extract of *Cocos nucifera* present in the amount of 40% by weight.

2. A cream formulation for topical use in humans in the management of pressure ulcers, wherein an oil phase of which comprises:

a) an extract of *Pongamia pinnata* ranging from 0.5% to 2.5% by weight;
b) an extract of *Lawsonia alba* ranging from 0.5% to 1.5% by weight;
c) an extract of *Datura alba* ranging from 0.2% to 1% by weight; and
d) an extract of *Cocos nucifera* ranging from 3% to 10% by weight.

3. The cream formulation of claim 2, the oil phase of which comprises:
   a) the extract of *Pongamia pinnata* present in the amount of 1.5% by weight;
   b) the extract of *Lawsonia alba* present in the amount of 1.0% by weight;
   c) the extract of *Datura alba* present in the amount of 0.6% by weight; and
   d) the extract of *Cocos nucifera* present in the amount of 7.0% by weight.

4. An oil for topical use in providing bleeding control comprising:
   a) an extract of *Pongamia pinnata* present in the amount of 15% by weight
   b) an extract of *Lawsonia alba* present in the amount of 10% by weight;
   c) an extract of *Datura alba* present in the amount of 6% by weight; and
   d) an extract of *Cocos nucifera* present in sufficient quantity.

* * * * *